United States Patent
Glaser et al.

(10) Patent No.: US 6,446,497 B1
(45) Date of Patent: Sep. 10, 2002

(54) RECIPROCATING MACHINE WITH OPERATING PARAMETER SENSOR

(75) Inventors: Josef Glaser, Graz (AT); Klaus-Christoph Harms, Graz (AT); Wolfgang Kling, Graz (AT); Michael Rasser, Graz (AT); Karl Wojik, Graz (AT)

(73) Assignee: AVL List GmbH, Graz (AU)

( * ) Notice: Subject to any disclaimer, the term of this patent is extended or adjusted under 35 U.S.C. 154(b) by 5 days.

(21) Appl. No.: 09/691,319

(22) Filed: Oct. 18, 2000

(30) Foreign Application Priority Data

Oct. 18, 1999 (AT) ............................................. 723/99 U

(51) Int. Cl.⁷ ............................................. G01M 15/00
(52) U.S. Cl. ........................................ 73/116; 73/119 R
(58) Field of Search ................................. 73/116, 117.2, 73/117.3, 118.1, 119 R

(56) References Cited

U.S. PATENT DOCUMENTS

| | | | | |
|---|---|---|---|---|
| 4,730,484 A | * | 3/1988 | Olschefski | ................ 73/119 R |
| 5,321,759 A | * | 6/1994 | Yuan | ........................ 381/71.12 |
| 5,359,662 A | * | 10/1994 | Yuan et al. | ............... 381/71.12 |
| 5,386,372 A | * | 1/1995 | Kobayashi et al. | ......... 700/280 |
| 5,386,472 A | * | 1/1995 | Pfaff et al. | ................ 381/71.12 |
| 5,396,703 A | * | 3/1995 | Rice | ........................ 29/407.08 |
| 5,404,643 A | * | 4/1995 | Rice | ........................ 29/407.02 |
| 5,965,806 A | * | 10/1999 | Antcliff et al. | ................ 73/116 |

* cited by examiner

*Primary Examiner*—Eric S. McCall
(74) *Attorney, Agent, or Firm*—Sonnenschein, Nath & Rosenthal

(57) ABSTRACT

A reciprocating machine with a friction bearing crank mechanism having a monitoring device monitoring operating parameters of the friction bearings of the crank mechanism via at least one sensor which is in connection with an evaluation device. At least one sensor is disposed near a part of the crank mechanism which moves in operation relative to the machine's housing. The connection of the sensor with the evaluation device is guided at least in part via the crankshaft. This provides a simple and effective monitoring option for the friction bearings of the crank mechanism and for other machine-specific parameters.

25 Claims, 1 Drawing Sheet

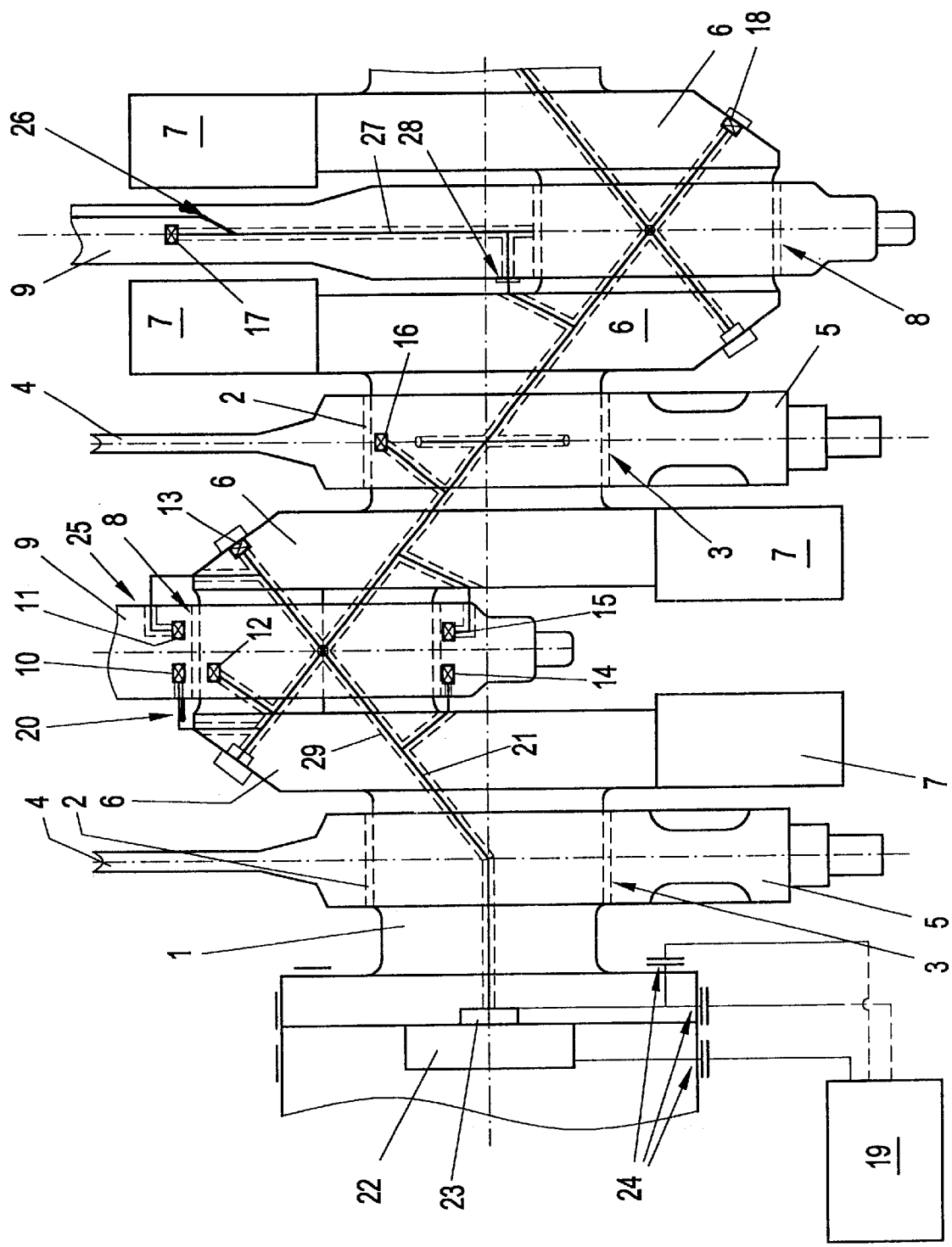

RECIPROCATING MACHINE WITH OPERATING PARAMETER SENSOR

CROSS-REFERENCES TO RELATED APPLICATIONS

This application claims the benefit of foreign priority Austrian Patent No. GM 723/99, filed Oct. 18, 1999.

BACKGROUND OF THE INVENTION

The invention relates to a reciprocating machine with a friction bearing crank mechanism and a monitoring device for monitoring operating parameters of the friction bearings of the crank mechanism via at least one sensor associated with an evaluation device.

The crank mechanism, and in particular a crankshaft with connecting rods and pertaining bearings, is the mechanical hub of a reciprocating machine, such as a combustion engine or a compressor. The forces generated by all cylinders act on the crankshaft and its connecting rods and bearings, adding up to the total power output of the reciprocating machine. Therefore, diagnostic monitoring of the mechanism is particularly important. The invention is based on the premise that the beginning of a malfunction of individually disposed bearings or cylinders can be detected relatively isolated to a particular area.

It is known in the art that bearing defects can be detected by acoustic emission as the defect begins and increases in severity, particularly with high-frequency sound or ultrasound. See, for example Acoustic Emission Testing (Nondestructive Testing Handbook; Vol. 5) by Ronnie K. Miller, Paul McIntire, American Society for Nondestructive Testing, 1987; Diagnostic of sliding pairings by means of sound emission analysis, by A. Sturm, S. Kuhlemann, Mechanical Engineering Berling 34 (1985) 3, pages 129–132; Method and arrangement for detecting the cause of wearing symptoms in friction bearings, by A. Sturm et al., DE 41 23 576 A1 & DE 40 28 559 A1.

Sensors for structure-borne sound having a piezo-electrical measuring element are usually used for analyzing the effect of sound emission on solid body structures. However, resistive, capacitive, inductive, piezo-magnetic or optical sensors for structure-borne sound can also be used. A comparison is made between "active" sensors, which require no auxiliary energy, and "passive" sensors, which typically have to be supplied with electrical current or a stimulating light. Generally, the sensors are designed to be mountable on the structure surfaces and to receive structure-borne sound signals transmitted by the structure that reach the surface of the structure. There are, however, differences in the directional characteristics and in the modal sensitivity of the sensors. For example, a sensor can be designed to detect sound waves arriving radially versus axially with a longitudinal polarization or with a transversal polarization in a certain direction.

Errors in the operation of individual cylinders of an internal combustion engine, such as spark failure, knocking or differences in performance as compared to the performance of other cylinders, can be detected by a standard indication method based on measured gas pressures in the combustion chamber, and can also be used for individual cylinder control and monitoring.

Disadvantages of known methods and devices include the fact that the monitoring sensors usually have to be mounted on the exterior of the static structures, and therefore they are far removed from the hub of the mechanical action, i.e. the crankshaft and bearings. This results in inferior detection of beginning bearing defects and of errors in individual cylinder behavior.

Typical mounting of sound emission sensors on the exterior of components having structure-borne sound contact with the static exterior of bearing-structures causes a significant weakening in the signal and inferior localized sound source differentiation because of long sound paths relative to the wavelength of the high-frequency sounds. Both of the above effects result in an undesirable strength ratio between the wanted signal and the underground or interfering signal, and therefore in an inferior monitoring capability. Furthermore, such apparatus is only able to monitor the main bearings. The apparatus is not able to monitor the connecting rod bearings because the sound signals generated in the connecting rod bearings are weakened on their way to the sensors by the complex structures, joints and lubricating oil films of the crank mechanism and the housing. In some instances, the sound signals are weakened to the point of being virtually unusable.

Using combustion chamber pressure indicators for indicating the behavior of individual cylinders suffers from the extreme stress to which the sensors are subjected. At least the more cost-effective models typically do not provide adequate operational reliability and life-expectancy for monitoring functions, whereby alternative solutions need to be found.

An objective of the present invention is to overcome one or more of the aforementioned disadvantages of apparatus known in the art.

SUMMARY OF THE INVENTION

At least one sensor is positioned near the friction bearings to be monitored in the crank mechanism that moves relative to the machine's housing, and the sensor's connection with the evaluation device is guided, at least in part, via the crankshaft. The sensor is mounted in close proximity with the event to be monitored whereby it can be reliably located or detected and analyzed. By guiding the sensor signals out via the crankshaft, the structural element, which is mechanically highly stable, can be advantageously utilized and it can also be provided, for example, that individual signal lines are disposed in the lubricant bores, which are usually present in the crankshaft. This provides a fairly simple apparatus for reliably monitoring the friction bearings in addition to various measured variables that affect the crank mechanism.

In another embodiment of the present invention, a non-contact, preferably capacitive, transmission device is provided for feeding the sensor signals in and/or out of the connecting path that runs in or on the crankshaft, and the transmission device preferably operates without any auxiliary energy. In such embodiment, in the proximity of the connecting rod bearings on the connecting rod or the bearings associated therewith, for example, sensors can be provided which, via a capacitive transmission device or other medium transmit respective measuring signals to the crankshaft from where they are led to the outside, for example, via signal lines present in the lubricating oil bores, for example in the area of the toothed rim on the flywheel where, again via a non-contact transmission device, the output to the monitoring device can take place. This allows continuous monitoring of the connecting rod bearing, for example, where the respective measuring signals can be transmitted to the outside quasi continuously.

In another embodiment of the present invention at least one sensor is formed as a sensor for structure-borne sound for high-frequency sound waves which is advantageous for detecting the beginning of bearing damage.

In another embodiment of the invention, at least one sensor is designed for detecting low-frequency mechanical tensions and deformations and it is preferably disposed on the connecting rod bearing, thus allowing the connecting rod stress to be measured so as to provide a measure for the combustion chamber pressure in the pertaining cylinder, and thus allowing an evaluation of the individual cylinders of an internal combustion engine.

In a further embodiment of the invention, at least one sensor is designed for detecting low-frequency hydraulic lubricating oil pressure on at least one friction bearing of the crank mechanism. This allows both the lubricating oil pressure and the bearing play, and thus wear and tear associated therewith, to be monitored.

In another embodiment of the invention, at least one sensor is designed as a combination sensor for detecting various measured variables, both low-frequency and high-frequency, for joint transmission of the combined signal portions to the evaluation device.

It is particularly advantageous to design the monitoring sensor as a combination sensor for sensing ultrasound emission and for sensing lubricating oil pressure present on the bearing. In addition to the sensitivity for the low-frequency lubricating oil pressure and high-frequency sound emission of the adjacent bearings this is particularly advantageous for obtaining an additional high sensitivity for the sound emission of the lubricating oil which is cavitation-related, for example.

The high-frequency signal portion represents the received structure-borne sound and the low-frequency portion represents a further physical measured variable, and the two signal portions are combined and transmitted together. At the time they are evaluated, the two signal portions will be separated according to frequency and further processed. The low-frequency measured variable, for example, can characterize the forces transmitted by the connecting rod via the connecting rod bearing to the crankshaft, so that the measuring signal will indicate cylinder-specifically, among others, spark failure, knocking and any deviations in behavior as compared to the behavior of the remaining cylinders in an internal combustion engine. However, the low-frequency measured variable can also characterize the lubricating oil pressure present on the bearing, so that indications for an inadequate lubricating oil supply and/or lubrication can be detected in the measuring signal.

In another embodiment of the invention at least one sensor can be embedded in the solid body structure of the crank mechanism, preferably in the area of a friction bearing to be monitored, of a crank arm or the connecting rod. As a result of the relatively good sound transmission in the compact structure of the crankshaft, a sensor for structure-borne sound imbedded in the crankshaft will supply dominant signals originating from the closest sound sources. Therefore, one sensor may be sufficient for monitoring the adjacent main bearings and connecting rod bearings. By means of a correlative analysis of the signals of a sensor with the signals of at least a second sensor, such as the next closest sensor, which is mounted in the adjacent crank arm, for example, the sound source can be located. Thus, with this method, it is possible to differentiate which bearing the detected signals originate on, thereby advantageously saving some sensors and thus expenses, provided that the quality of the sound transmission in the crankshaft is adequate.

Accordingly, virtually no additional projecting parts are necessary on the crank mechanism. The sensor is fully encompassed by the measured object and its temperature, and thus it is well protected. Furthermore, the sensor can be optimally adapted to its measuring function. In case of a sensor for structure-borne sound, for example, a high sensitivity and selectivity can be achieved with regard to the longitudinal and transversal oriented sound waves present in the interior of the structure. Also, the style of the sensor and the method of mounting can be designed advantageously for a certain directional characteristic and mode sensitivity, thereby achieving an optimal utilization sensitivity and interfering signal suppression for the selected location where it is mounted and for the locations of interest of ultrasound emission.

A further embodiment is particularly advantageous in which a sensor is designed as a stopper for a boring on the crank arm leading to an exterior for supplying lubricating oil to the friction bearings. This allows a simple design and mounting of the monitoring sensor.

In another embodiment of the invention, at least one sensor is designed as a temperature sensor allowing both low and, when required, temporarily higher defined temperature monitoring of the bearings.

In a particularly advantageous embodiment of the invention electrical or electronic components are provided on the sensor, or at least near the location where the sensor is mounted on the crank mechanism for at least partial signal processing or handling, which components are connected both to the sensor and to the evaluation or monitoring device. Accordingly, at least a portion of signal processing can take place in direct proximity of the sensor with the known related advantages, which makes it considerably easier and less critical to further transmit the signal. For example, an electric filter connection for suppressing interfering frequency components of the sensor signal can also be integrated in the sensor itself, or a high-pass filtering for suppressing low-frequency signal components can take place directly at a sensor for structure-borne sound. On the other hand, with a sensor for a low-frequency measured variable, a low-pass filtering for suppressing high-frequency signal components can occur. In the case of a combination sensor, for example, the high-frequency and the low-frequency signals can be filtered by separate measuring elements, in one case high-pass filtered and in the other case low-pass filtered, before they are combined. Preferably, such electric filter connections contain only passive components (such as resistors, capacitors and inductors, for example) which will not require an additional voltage supply for the components.

In a further preferred embodiment of the invention, a common connection path to the evaluation device can be provided for transmitting the combined signals of multiple sensors during general monitoring wherein a diagnostic association of the signals to the signal-emitting sensor is not required.

In an advantageous embodiment of the invention the sensors themselves can comprise electrically active, preferably piezo-electrical, measuring elements with which the most varied measuring functions can reliably and accurately be carried out because such sensors are also relatively insensitive to high temperatures, vibrations and similar operating conditions.

BRIEF DESCRIPTION OF THE DRAWINGS

The invention is described in more detail by means of a drawing of a schematic section of a reciprocating machine with a friction bearing crank mechanism, in accordance with the present invention.

DETAILED DESCRIPTION OF THE PREFERRED EMBODIMENT

Only the left side of a multi-cylinder reciprocating machine is shown whose crankshaft 1 is disposed in main bearings 3 in the form of friction bearings 2 (only the two left ones of which are shown). The top section of the friction bearings 2 in the drawing is disposed on bearing walls 4 of the machine housing or crankcase or cylinder block, which is not shown in detail. The bottom sections are connected with bearing straps 5 which are usually screwed on so as to be removable. Between the crank arm 6 with counterweights 7 connecting rod bearings 8 are provided for connecting rods 9, which are only suggested, where the connecting rod bearings 8 themselves again are separate, similarly as described with regard to the main bearings 3.

A number of sensors (referenced 10 to 18) are shown schematically, each near the friction bearings 2, 3, 8 to be monitored on parts of the crank mechanism which are moving relative to the machine housing, which is represented here by the bearing walls 4, which parts are connected, at least partially, via the crankshaft 1 with an evaluation device 19 located on the outside.

The sensor 10 in the area of the left connecting rod bearing 8 is connected via a transmission device 20, for example capacitive by means of two concentric cylinder surfaces or a respective full cylinder and an associated partial cylinder with the connecting line 21 continuing in the crankshaft 1 (for example in the oil bore 29), which line 21 is then connected on the left side with a signal processing and amplification unit 22, 23. Unit 22, 23 can then be in connection with evaluation device 19 via a wireless transmission device 24, which is merely suggested (for example passive, capacitive or active via radio).

Sensor 11, for example after modifying the connecting rod form so as to obtain the space for signal transmission by means of the transmission device 25, can be disposed at a location on the connecting rod bearing different from the location of sensor 10. The signal can then be transmitted further, similarly as described for sensor 10.

Sensor 12 on the crankshaft side of the connecting rod bearing requires no non-contact transmission and can be directly contacted to the exterior, such as via lubricating oil bore 29 or a connecting line 21 therein.

The same applies to sensor 13 which is installed in the area of a screw plug of oil bore 29 or in oil bore 29 itself. Sensors 14 and 15, again similar to sensors 10 and 11 as described above, are disposed on the connecting rod side of the connecting rod bearing and accordingly have to transmit their signals contact-less into the crankshaft, and from there again via connecting line 21, for example.

Sensor 16 on the crankshaft side of the right main bearing 3 can be contacted directly via connecting line 21, similarly as described for sensors 12 and 13.

Sensor 17 in the connecting rod (and additional sensors provided when required via line 26 in the area of the connecting rod eye, which is not shown) is connected via a connecting line 27 with a non-contact transmission device 28 which, for example, by means of flat ring areas, comb structures, or the like, enables a passive or active signal transmission into the crankshaft and from there to the outside via connecting line 21.

Sensor 18 again is installed similar to sensor 13 in the area of a screw plug of lubricating oil line 29 in the crankshaft or in said screw plug itself and can be connected with the outside via connecting lines 21 running in or parallel to the oil bores.

In addition to the exemplary embodiment which is shown and discussed, some individual sensors only, or considerably more of them, can be provided and contacted or connected with signal processing and amplification unit 22, 23 or evaluation device 19 based on the respective circumstances. Also, departing from the embodiment shown, at least some of the sensors could have directly associated or adjacent signal processing devices or the like. Furthermore, it is feasible both to contact individual or all sensors via a common connecting line and to connect individual or all sensors via separate such connecting lines with the evaluation device. The design and the working principle of the individual sensors is freely selectable within a wide range and can be adjusted to individual needs. Overall, this provides a very simple and reliable monitoring option for the function of the friction bearings of the crank mechanism or other machine-specific variables.

As is apparent from the foregoing specification, the invention is capable of being embodied with various alterations and modifications which may differ from those that have been described in the specification and description provided herein above. It should be understood that the claims shall cover all such modifications that reasonably and properly come within the scope of my contribution to the art.

We claim:

1. A reciprocating machine having a housing and comprising:
    a crank mechanism having a crankshaft and friction bearing;
    an evaluation device;
    at least one sensor for monitoring operating parameters of said friction bearings and emitting signals to be transmitted to said evaluation device via a connection therewith;
    said at least one sensor being positioned near said friction bearings on a portion of said crank mechanism which moves relative to said housing of said reciprocating machine during operation of said reciprocating machine; and
    said connection of said at least one sensor with said evaluation device being at least partially accomplished via said crankshaft of said crank mechanism.

2. A reciprocating machine according to claim 1 further comprising a non-contact transmission device for transmitting signals between said at least one sensor and said crankshaft.

3. A reciprocating machine according to claim 2 further comprising a non-contact capacitive transmission device for transmitting said sensor signals to and from said crankshaft.

4. A reciprocating machine according to claim 2 further comprising a transmission device without auxiliary energy for feeding said sensor signals to and from said crankshaft.

5. A reciprocating machine according to claim 1 wherein said at least one sensor is designed as a sensor for structure-borne sound comprising high-frequency sound waves.

6. A reciprocating machine according to claim 1 wherein said at least one sensor is designed for detecting lower frequency mechanical tensions and deformations.

7. A reciprocating machine according to claim 6 wherein said at least one sensor is positioned on bearings for a connecting rod in said reciprocating machine.

8. A reciprocating machine according to claim 1 wherein said at least one sensor is designed for detecting low frequency hydraulic lubricating oil pressure on at least one of said friction bearings.

9. A reciprocating machine according to claim 1 wherein said at least one sensor is a combination sensor for detecting both high frequency and low frequency measured variables and for jointly transmitting combined signals to said evaluation device.

10. A reciprocating machine according to claim 9 wherein said combination sensor is designed both for detecting high frequency ultrasound emissions of said friction bearings and for detecting low frequency forces transmitted by said friction bearings.

11. A reciprocating machine according to claim 9 wherein said combination sensor is designed both for detecting high frequency ultrasound emissions of said friction bearings and for detecting lubricating oil pressure in said friction bearings.

12. A reciprocating machine according to claim 1 wherein said at least one sensor is embedded in a solid body structure of said crank mechanism.

13. A reciprocating machine according to claim 9 wherein said at least one sensor is embedded in a solid body structure of said crank mechanism.

14. A reciprocating machine according to claim 13 wherein said at least one sensor is embedded in said solid body structure of said crank mechanism in an area of friction bearings to be monitored.

15. A reciprocating machine according to claim 13 wherein said at least one sensor is embedded in said solid body structure of said crank mechanism in an area of a crank arm.

16. A reciprocating machine according to claim 13 wherein said at least one sensor is embedded in said solid body structure of said crank mechanism in an area of a connecting rod.

17. A reciprocating machine according to claim 13 wherein said at least one sensor is designed as a sealing stopper for a bore on a crank arm for supplying lubrication oil to said friction bearings.

18. A reciprocating machine according to claim 1 wherein said at least one sensor is a temperature sensor.

19. A reciprocating machine according to claim 1 further comprising electrical components mounted on said crank mechanism and positioned in proximity to said sensor, said electrical components connected to said sensor and to said evaluation device, and said electrical components capable of at least partially processing signals.

20. A reciprocating machine according to claim 1 further comprising electronic components mounted on said crank mechanism and positioned in proximity to said sensor, said electronic components connected to said sensor and to said evaluation device, and said electronic components capable of at least partially processing signals.

21. A reciprocating machine according to claim 1 wherein signals of multiple sensors are combined and transmitted to said evaluation device via a common connecting line.

22. A reciprocating machine according to claim 1 wherein said at least one sensor comprises electrically active measuring elements.

23. A reciprocating machine according to claim 22 wherein said at least one sensor comprises piezo-electrical measuring elements.

24. A reciprocating machine comprising:

a crank mechanism having a housing, a crankshaft and friction bearings, at least a portion of said crank mechanism movable with respect to said housing of said crank mechanism;

a sensor associated with said crank mechanism and operable to sense structure-borne sound comprising sound waves of varying frequencies; and an evaluation device connected to said sensor, said connection at least partially guided by said crankshaft.

25. A reciprocating machine according to claim 24 further comprising electronic components mounted on said crank mechanism and positioned in proximity to said sensor, said electronic components connected to said sensor and to said evaluation device, and said electronic components capable of at least partially processing signals corresponding to said sound waves of varying frequencies.

* * * * *